United States Patent [19]

Schossler

[11] Patent Number: 4,891,156

[45] Date of Patent: Jan. 2, 1990

[54] N-ALKYL-BENZENESULPHONAMIDE COMPOSITIONS

[75] Inventor: Willi Schossler, Cologne, Fed. Rep. of Germany

[73] Assignee: Bayer Aktiengesellschaft, Leverkusen, Fed. Rep. of Germany

[21] Appl. No.: 172,103

[22] Filed: Mar. 23, 1988

[30] Foreign Application Priority Data

Apr. 7, 1987 [DE] Fed. Rep. of Germany ....... 3711689

[51] Int. Cl.$^4$ ................................................. C23G 5/00
[52] U.S. Cl. ..................................................... 252/364
[58] Field of Search ............................. 252/364; 564/84

[56] References Cited

U.S. PATENT DOCUMENTS 2,214,405  9/1940  Coffman .
4,064,168 12/1977  Kotlarchik et al. ................... 564/84
4,629,680 12/1986  Iwasaki et al. ....................... 430/286
4,657,942  4/1987  Iwasaki et al. ....................... 430/286

FOREIGN PATENT DOCUMENTS 0007623  2/1980  European Pat. Off. .
0069278  1/1983  European Pat. Off. .
2617180 11/1976  Fed. Rep. of Germany .

Primary Examiner—Mary C. Lee
Assistant Examiner—Catherine S. K. Scalzo
Attorney, Agent, or Firm—Sprung Horn Kramer & Woods

[57] ABSTRACT

N-Alkyl-benzenesulphonamides, the alkyl group of which is open-chain $C_1$–$C_{12}$-alkyl or $C_5$–$C_7$-cycloalkyl and the benzene nucleus of which can be substituted by $C_1$–$C_4$-alkyl, can be heat-stablized by 10–1,000 ppm of one or more 2-mercapto-benzimidazole compounds of the formula

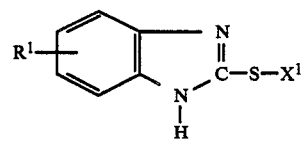

wherein
$R^1$ denotes hydrogen of a $C_1$–$C_4$-alkyl group and
$X^1$ denotes hydrogen or 1 equivalent of the metals Zn, Cd or Mn(II).

Such stabilized N-alkyl-benzenesulphonamides can be used as plasticizers for polymers having polar groups.

7 Claims, No Drawings

N-ALKYL-BENZENESULPHONAMIDE COMPOSITIONS

BRIEF DESCRIPTION OF THE INVENTION

The invention relates to N-alkyl-benzenesulphonamides, the alkyl group of which is open-chain $C_1$–$C_{12}$-alkyl or $C_5$–$C_7$-cycloalkyl and the benzene nucleus of which can be substituted by $C_1$–$C_4$-alkyl, containing 10–1,000 ppm of one or more 2-mercapto-benzimidazole compounds of the formula

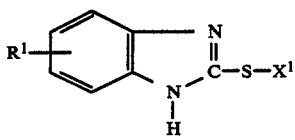

(I)

wherein
$R^1$ denotes hydrogen or a $C_1$–$C_4$-alkyl group and
$X^1$ denotes hydrogen or 1 equivalent of the metals Zn, Cd or Mn(II).

The invention thus relates to mixtures of 10–1,000 ppm of the said 2-mercapto-benzimidazole compound(s), relative to the total quantity of the mixture, and of the said N-alkyl-benzenesulfonamides as the remainder to make up to 100% of the total quantity of the mixture.

DETAILED DESCRIPTION OF THE INVENTION

The N-alkyl-benzenesulfonamides here represent pure substances, such as they are obtained by the preparation processes described further below and subsequent working-up or purification. The purity is regularly 99.5% or higher, and in many cases 99.9%. Residual small impurities originate from the preparation process.

The said 2-mercapto-benzimidazole compounds represent stabilizers of the N-alkyl-benzenesulphonamides, for example against thermally caused deterioration. The invention thus relates to N-alkyl-benzenesulphonamides of the said type, which are stabilized by the said 2-mercaptobenzimidazole compounds.

Examples of the N-alkyl groups of the benzenesulphonamides are open-chain groups having 1–12 C-atoms and cyclic groups having 5–7 C-atoms, such as methyl, ethyl, propyl, i-propyl, n-butyl, i-butyl and the straight-chain or branched amyls, hexyls, heptyls, octyls, decyls or dodecyls, as well as cyclopentyl, methylcyclopentyl, cyclohexyl and methylcyclohexyl. In a preferred manner, the N-alkyl groups are open-chain groups having 1–8 C atoms or, respectively, cyclohexyl; in a particularly preferred manner, they are open-chain groups having 1–6 C atoms or, respectively, cyclohexyl.

Further preferred N-alkyl groups are those having 4–8 C atoms. n-Butyl, n-hexyl and 2-ethylhexyl are very particularly preferred N-alkyl groups.

The $C_1$–$C_4$-alkyl groups in the benzene nucleus of the sulphonamides or in the benzimidazole compounds are independently of one another, for example, methyl, ethyl, propyl, i-propyl, butyl or i-butyl preferably methyl or ethyl and particularly preferably methyl. In the very particularly preferred manner, the benzene nucleus of the sulphonamides does not carry any substituents.

Examples of metal cations are those of Zn, Cd or Mn(II), preferably of Zn or Mn(II) and particularly preferably of Zn.

In a preferred manner, 2-mercapto-benzimidazole compounds of the formula

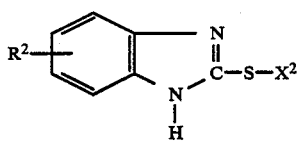

(II)

may be mentioned, wherein
$R^2$ denotes hydrogen, methyl or ethyl and
$X^2$ denotes hydrogen or 1 equivalent of the metals Zn or Mn(II).

In a particularly preferred manner, 2-mercaptobenzimidazole compounds of the formula

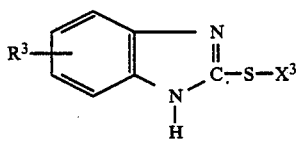

(III)

may be mentioned, wherein
$R^3$ denotes hydrogen or methyl and
$X^3$ denotes hydrogen or ½ $Zn^{2+}$.

Examples of compounds of the formula (I), (II) and (III) are: 2-mercapto-4-methyl-benzimidazole, 2-mercapto-5-methyl-benzimidazole, the isomer mixture of 2-mercapto-4-methyl- and 2-mercapto-5-methyl-benzimidazole, 2-mercapto-benzimidazole or their zinc salts, preferably the isomer mixture of 2-mercapto-4-methyl- and 2-mercapto-5-methyl-benzimidazole and 2-mercapto-benzimidazole, and particularly preferably 2-mercapto-benzimidazole.

The 2-mercapto-benzimidazole compound(s) is or are present in the stabilized N-alkyl-benzenesulphonamides according to the invention in a quantity of 10–1,000, preferably 15–300 and particularly preferably 15–200 ppm, relative to the total quantity of the mixture of the said 2-mercapto-benzimidazole compounds and the said N-alkyl-benzenesulphonamides. The stabilizing action is frequently already sufficient in the range of 15–100 and even 15–50 ppm. Of course, larger quantities than 1,000 ppm can also be used, but they do not show an additional effectiveness.

The mixture constituents of the stabilized mixture according to the invention are known and can be prepared by known processes. Thus, it is generally known to prepare sulphonic acid amides by condensing sulphonic acid chlorides with amines in water or in an inert solvent (for example benzene or acetone) in the presence of an acid acceptor (for example sodium hydroxide solution, sodium bicarbonate, calcium carbonate, sodium sulphite, sodium acetate in glacial acetic acid, a second mole of the amine, pyridine or others) (Ullmanns Encyclopädie der technischen Chemie [Ullmann's Encyclopedia of Industrial Chemistry], Volume 8 (1974), page 418, left-hand column, 3rd paragraph, and Houben-Weyl, Methoden der organischen Chemie [Methods of Organic Chemistry], Volume 9 (1955), pages 609–616). Within the scope of this general knowledge, N-n-butyl-benzenesulphonamide, for example, can be prepared from benzenesulphochloride and n-butylamine in the presence of alkali (Beilstein, Volume 11 (H), page 41) or from benzenesulphochloride and 2 moles of butylamine in ethanol (Beilstein, Volume 11 (E III), page 54; Rec. Trav. Chim. Pays-Bas, Volume 50 (1931), page 52, 1st paragraph).

For working up liquid sulphonamides, these can, if appropriate in the form of a solution in an organic solvent such as benzene, be washed with water, dried with drying agent (for example sodium sulphate), filtered and then distilled. If necessary, the distillate can be treated with activated charcoals, such as Norit, and filtered once more (Ind. Eng. Chem., Volume 46 (1954), pages 587 and 590). Furthermore, liquid sulphonamides can, after they have been prepared in an aqueous system, be separated off as an oil layer. To remove water, this oil layer can be heated in vacuo, whereupon a very small quantity of inorganic salt (for example sodium chloride, if the preparation was carried out in the presence of NaOH or $NaHCO_3$), is filtered off with suction from the oil (Houben-Weyl, Methoden der organischen Chemie [Methods of Organic Chemistry], Volume 9 (1955), page 610, penultimate paragraph). When removing the water, an adsorbent, for example activated charcoal or bleaching earth, can optionally be used in addition. Finally, distillation of the crude sulphonamide under a reduced pressure is possible. Colourless to pale yellowish coloured N-alkyl-benzenesulphonamides having Hazen colour numbers of <5 to 15 can be obtained by these processes. Sulphonamides, the freezing points of which are above room temperature but below the boiling point of water, can be worked up in the same way as oils, if the working temperature is correspondingly adapted.

Solid sulphonamides can be worked up in the known manner by the methods known for solids.

The 2-mercapto-benzimidazole compounds present in the mixture according to the invention are likewise known and can be prepared, for example, by reacting an optionally substituted o-phenylenediamine with carbon disulphide at an elevated temperature, with cyclization and elimination of $H_2S$. The metal compounds are obtained by further reaction with suitable metal salts (Ullmanns Enzyklopädie der Technischen Chemie [Ullmann's Encyclopedia of Industrial Chemistry], 4th Edition, Volume 23 (1983), pages 193, 195 and 196).

The N-alkyl-benzenesulphonamides according to the invention, the alkyl group of which is open-chain $C_1$–$C_{12}$-alkyl or $C_5$–$C_7$-cycloalkyl and the benzene nucleus of which can be substituted by $C_1$–$C_4$-alkyl, containing 10–1,000 ppm of one or more 2-mercapto-benzimidazole compounds of the formula

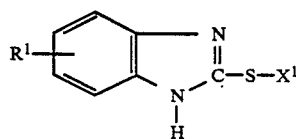

wherein
$R^1$ denotes hydrogen or a $C_1$–$C_4$-alkyl group and
$X^1$ denotes hydrogen or 1 equivalent of the metals Zn, Cd or Mn(II), can be prepared, for example, in such a way that the said quantity of the 2-mercapto-benzimidazole compound(s) is added to and homogeneously mixed with the N-alkyl-benzenesulphonamides prepared in the conventional manner from benzenesulphochlorides, the benzene nucleus of which can be substituted by $C_1$–$C_4$-alkyl, and $C_1$–$C_{12}$-alkylamines or $C_5$–$C_7$-cycloalkylamines, or that such a quantity of one or more of the 2-mercaptobenzimidazole compound(s) is added to such N-alkyl-benzenesulphonamides before or during their working-up after the said preparation that, allowing for the losses in the working-up process, the said quantity of the 2-mercaptobenzimidazole compound(s) remains in the N-alkyl-benzenesulphonamides.

Accordingly, 2-mercapto-benzimidazole compounds of the formulae (I), (II) and/or (III) can be added to the crude N-alkyl-benzenesulphonamides, for example before the removal of water if the preparation took place in an aqueous system or washing with water was carried out, the water can then be removed in vacuo in the presence of adsorbents and the mixture can then be filtered. However, the 2-mercapto-benzimidazole compounds can also be added to the N-alkylbenzenesulphonamides after the latter have been distilled under a reduced pressure.

In this case, the 2-mercapto-benzimidazole compounds can be added in the pure form or as a solution of higher concentration in the N-alkyl-benzenesulphonamide which is to be stabilized. In the case where the working-up method of the crude N-alkyl-benzenesulphonamides starts from their solution in an organic solvent (for example in benzene or acetone), the 2-mercapto-benzimidazole compounds can also be added in the form of a solution in such an organic solvent, whereupon the working-up steps described further above are carried out.

N-alkyl-benzenesulphonamides as such, that is to say not in the form of the mixture according to the invention as described above, have already been used as plasticizers for polymers having polar groups (Ind. Eng. Chem., Volume 46 (1954), page 590, right-hand column, 2nd and 3rd paragraphs). It was found here that polymers plasticized with N-alkyl-benzenesulphonamides showed very different discolorations on heat treatment at 160° C. It was not possible to establish a precise dependence on the N-alkyl group.

The N-alkyl-benzenesulphonamides obtained by the working-up methods described above also show very different heat stabilities without any obvious reason and without a dependence on the individual working-up variant. The inadequate heat stability manifests itself in severe discoloration of the heat-treated N-alkyl-benzenesulphonamide and makes the latter unsuitable for the production of colourless plasticized polymers (see comparison examples included in the illustrative examples).

On the other hand, it is known to use N-alkyl-benzenesulphonamides, for example N-n-butyl-benzenesulphonamide, as plasticizers for polymers having polar groups, such as, for example, nitrocellulose, acetylcellulose or polyamides (Ullmanns Enzyklopädie der Technischen Chemie [Ullmann's Encyclopedia of Industrial Chemistry], 4th Edition, Volume 24 (1983), pages 371 and 372). For example, N-n-butyl-benzenesulphonamide confers a higher elasticity on polyamides, when they are processed into mouldings such as shoe soles, shoe heels and other industrial parts. Such polyamide mouldings plasticized with N-n-butyl-benzenesulphonamide, even if they have fully dried out, remain supple and do not become brittle, as is observed in the case of polyamide mouldings which have been elasticized exclusively with water. Such polyamide mouldings should, independently of their production at an elevated temperature by injection-moulding or extrusion and independently of the use of N-alkyl-benzenesulphonamides, any thermal instability of which is not immediately obvious, always result as clear colourless products. For this purpose, N-alkyl-benzenesulphonamides of always uniform heat stability are highly desirable.

There has been no lack of attempts by us to prepare N-alkyl-benzenesulphonamides in a uniformly heatstable form. Thus, for example, additions of 4,4'-dihydroxydiphenyl, 2,2-bis-(4-hydroxyphenyl)-propane, 2,2-bis-(4-hydroxycyclohexyl)-propane, octadecyl 3-(3,5-di-tert.-butyl-4-hydroxyphenyl)-propionate, pentaerythrityl tetrakis-[3-(3,5-di-tert.-butyl-4-hydroxyphenyl)-propionate] and 2,6-di-tert.-butyl-4-methylphenol were applied in large quantities, without achieving an adequate heatstabilizing effect. The N-alkyl-benzenesulphonamides resulting from these experiments were therefore unsuitable for use as plasticizers. The effectiveness of the addition according to the invention of 2-mercapto-benzimidazole compounds in the small quantities indicated is therefore extremely surprising.

The invention also relates to the use of the N-alkyl-benzenesulphonamides, stabilized according to the invention, as plasticizers for polymers having polar groups, for example as plasticizers for nitrocellulose, acetylcellulose, cellulose acetopropionate, cellulose acetobutyrate, polyvinyl chloride, polyesters, polyamides and the like. In particular, the invention relates to the use of the N-alkyl-benzenesulphonamides stabilized according to the invention as plasticizers for polyamides.

The stabilized N-alkyl-benzenesulphonamides (that is to say the mixture according to the invention of the N-alkyl-benzenesulphonamides mentioned and the 2-mercapto-benzimidazole compounds likewise mentioned) can, when they are used, optionally be employed together with other additives, such as stabilizers for the polymer, colouring agents and other additives conventional in polymer processing. In such cases, the mixture according to the invention is a mixture constituent of a larger mixture.

The testing of the heat stability of plasticizers by testing plasticized polymers obtained by injection-moulding or extrusion is involved and, because of the influence of parameters of the machines used for this purpose and the influence of the varying quality of the polymer, uncertain. It is therefore more reliable and more reproducible to heat-treat the plasticizer alone and to establish its quality independently of the other influences mentioned. For this purpose, samples of the plasticizer are heated for varying times at varying temperatures, and their colour change is then determined. These times and temperatures are in general adapted to the processing conditions of the plasticized polymers, including suitable safety margins where necessary.

In the examples which follow, the colour change of the heated samples was measured and reported with the aid of the Hazen colour scale defined up to a value of 500.

In the comparison examples, values frequently resulted which were higher than 500 Hazen and were therefore outside the ccale. Since, according to Analytical Chem., Volume 49 (1977), pages 524 and 525, there is a relationship between values determined spectrophotometrically and the Hazen scale, the extinction at 450 nm (cell $D=1$ cm, comparison measurement against the unheated sample) was measured in such cases. For correlation with such values outside the Hazen scale, the extinction was also measured for comparison on some samples which were inside the Hazen scale (indicated in brackets within the examples).

EXAMPLE 1

N-n-Butyl-benzenesulphonamide was prepared in the known manner by condensing benzenesulphochloride and n-butylamine in the presence of water and sodium hydroxide solution. After complete conversion of the benzenesulphochloride, the resulting oil was separated off from the aqueous phase, washed once more with water and again separated from the aqueous phase. 1% by weight each of activated charcoal and bleaching earth were added as adsorbents to the crude product in a glass apparatus, and the mixture was heated in vacuo to remove the water and then filtered. The N-n-butyl-benzenesulphonamide obtained had a purity of 99.9% and a colour number of 5 Hazen.

50 or 100 ppm of 2-mercapto-benzimidazole were added with stirring to this N-n-butyl-benzenesulphonamide, and the mixture was then heated for the times indicated in Table 1 to the temperatures indicated. An N-n-butylbenzenesulphonamide without an additive was heated for comparison. The Hazen colour numbers and some extinction values of the heat-treated samples were determined (Table 1).

TABLE 1

(Example 1): Hazen colour numbers and extinction values (in brackets) of heat-treated N—n-butylbenzenesulphonamide

| No. | Quantity of 2-mercapto-benzimidazole | 160° C. | | 170° C. | | | 190° C. |
|---|---|---|---|---|---|---|---|
| | | 2 hours | 3 hours | 1 hour | 2 hours | 3 hours | 1 hour |
| 1a | 100 ppm | 10 | 15 | 10 | 30 | 60 | 55 |
| 1b | 50 ppm | 30 | 50 | 25 | 80 (0.018) | 110 (0.027) | 90 (0.020) |
| 1c* | none | 330 | 500 | 300 | >500 (0.185) | >500 (0.275) | >500 (0.262) |

*comparison test not according to the invention

EXAMPLE 2

An N-n-butyl-benzenesulphonamide obtained similarly as in Example 1 was obtained in a purity of 99.9% and with a colour number of <5 Hazen. 10 to 50 ppm of 2-mercapto-benzimidazole were added with stirring to this N-n-butyl-benzenesulphonamide, and the mixture was then heated to 170° C. The colour numbers were determined after 0.25 and 1 hour. The heat stability of the N-n-butylbenzenesulphonamide without additive was determined for comparison. All the values are listed in Table 2.

TABLE 2

(Example 2): Hazen colour numbers of N—n-butyl-benzenesulphonamide heat-treated at 170° C.

| No. | Quantity of 2-mercapto-benzimidazole | 0.25 hour | 1 hour |
|---|---|---|---|
| 2a | 50 ppm | <5 | 5 |
| 2b | 25 ppm | <5 | 5 |
| 2c | 20 ppm | <5 | 5 |
| 2d | 10 ppm | 5 | 10 |
| 2e* | none | 130 | 400 |

*comparison test not according to the invention

EXAMPLE 3

20 ppm of 2-mercapto-benzimidazole (Vulkanox M ®, commercial product of Messrs. Bayer AG), of the isomer mixture of 4-methyl- and 5-methyl-2-mercapto-benzimidazole (Vulkanox MB-2, commercial product of Messrs. Bayer AG) and of the zinc salt of the said isomer mixture (Vulkanox ZMB-2 ®, commercial product of Messrs. Bayer AG) were added with stirring in each case to N-n-butyl-benzenesulphonamide obtained similarly as in Example 1 and having a purity of 99.9% and a colour number of <5 Hazen, and the mixtures were then heated to 170° C. After heat treatment for 1 hour, the colour numbers and some extinction values were determined. The heat stability of the N-n-butyl-benzenesulphonamide without additive was determined for comparison. All the values are listed in Table 3.

TABLE 3

(Example 3): Hazen colour numbers and extinction values (in brackets) of heat-treated N—n-butyl-benzenesulphonamide (1 hour, 170° C.) with 20 ppm of each of various additives.

| No. | Additive | Colour number |
|---|---|---|
| 3a | Vulkanox MB ® | 15 |
| 3b | Vulkanox MB-2 ® | 50 |
| 3c | Vulkanox ZMB-2 ® | 55 (0.013) |
| 3d* | none | >500 (0.160) |

*comparison test not according to the invention

Results comparable to those in Example 3c were obtained with the Mn(II) salts of 2-mercapto-benzimidazole and of the said isomer mixture. The wide fluctuation of the Hazen colour number of the heat-treated N-n-butyl-benzenesulphonamide without an additive shows chance events, which have not been elucidated, in the absence of stablization.

EXAMPLE 4

The procedure followed was as described in Example 1, but the purification of the crude N-n-butyl-benzenesulphonamide was carried out in a V4A stainless steel apparatus. The pure product obtained had a purity of 99.9% and a colour number of 5 Hazen. 10 to 1,000 ppm of 2-mercapto-benzimidazole were added with stirring to this pure N-n-butyl-benzenesulphonamide, and the mixtures were then heated to 170° C. The colour numbers and some extinction values were determined after 0.25 and 1 hour. The N-n-butyl-benzenesulphonamide thus purified was heat-treated without an additive for comparison. All the values are listed in Table 4.

TABLE 4

(Example 4): Hazen colour numbers and extinction values (in brackets) of N—n-butyl-benzenesulphonamide heat-treated at 170° C.

| No. | Quantity of 2-mercapto-benzimidazole | 0.25 hour | 1 hour |
|---|---|---|---|
| 4a | 1,000 ppm | <5 | 20 |
| 4b | 200 ppm | <5 | 30 |
| 4c | 100 ppm | <5 | 35 |
| 4d | 50 ppm | 10 | 35 |
| 4e | 10 ppm | 10 | 150 (0.037) |
| 4f* | none | 120 | >500 (0.390) |

*comparison test not according to the invention

EXAMPLE 5

The procedure followed was as described in Example 1, but the 2-mercapto-benzimidazole, in quantities from 100 to 400 ppm, relative to the crude product employed, was already added before the purification described. This gave products having purities of 99.9% and colour numbers of <5 Hazen. The stabilized N-n-butyl-benzenesulphonamides obtained were heated to 170° C. The colour numbers were determined after 0.25 and 1 hour (Table 5).

TABLE 5

(Example 5): Hazen colour numbers of N—n-butyl-benzenesulphonamide heat-treated at 170° C.

| No. | 2-mercapto-benzimidazole in the crude product | in the end product | 0.25 hour | 1 hour |
|---|---|---|---|---|
| 5a | 400 ppm | about 200 ppm | <5 | 5 |
| 5b | 200 ppm | about 45 ppm | 5 | 30 |
| 5c | 100 ppm | about 12 ppm | 5 | 120 |

EXAMPLE 6

The procedure followed was as described in Example 1, but the purification of the N-n-butyl-benzenesulphonamide after the second phase separation was carried out by direct fractional distillation in vacuo in a glass apparatus. This gave a product having a purity of 99.9% and a colour number of 15 Hazen. 50 ppm of 2-mercaptobenzimidazole were added with stirring to the distilled N-n-butyl-benzenesulphonamide, and the mixture was then heated for the times indicated in Table 6 to the temperatures indicated. The N-n-butyl-benzenesulphonamide was heated without an additive for comparison. The Hazen colour numbers and some extinction values of the heat-treated samples were determined (Table 6).

TABLE 6

(Example 6): Hazen colour numbers and extinction values (in brackets) of heat-treated N—n-butyl-benzenesulphonamide

| No. | Quantity of 2-mercapto-benzimidazole | 160° C. 3 hours | 160° C. 4 hours | 170° C. 1 hour | 170° C. 2 hours | 170° C. 3 hours | 190° C. 1 hour |
|---|---|---|---|---|---|---|---|
| 6a | 50 ppm | 40 (0.010) | 60 (0.014) | 30 | 45 | 90 (0.021) | 80 (0.019) |
| 6b* | none | >500 (0.185) | >500 (0.260) | 350 | 500 | >500 (0.260) | >500 (0.162) |

*comparison test not according to the invention

EXAMPLE 7

N-Methyl-benzenesulphonamide was prepared analogously to Example 1 by condensing benzenesulphochloride and aqueous methylamine in the presence of sodium hydroxide solution. After complete conversion of the benzenesulphochloride, the resulting oil was worked up as indicated in Example 1. The N-methyl-benzenesulphonamide obtained had a purity of 99.8% and a colour number of 5 Hazen.

50 ppm of 2-mercapto-benzimidazole were added with stirring to this N-methyl-benzenesulphonamide, and the mixture was then heated for the times indicated in Table 7 to the temperatures indicated. An N-methyl-benzenesulphonamide without an additive was heated for comparison. The Hazen colour numbers of the heat-treated samples were determined (Table 7).

TABLE 7

(Example 7): Hazen colour numbers of heat-treated N—methyl-benzenesulphonamide

| No. | Quantity of 2-mercapto benzimidazole | 170° C. 1 hour | 170° C. 3 hours | 190° C. 1 hour |
|---|---|---|---|---|
| 7a | 50 ppm | 25 | 50 | 50 |
| 7b* | none | 90 | 150 | 150 |

*comparison test not according to the invention

EXAMPLE 8

N-n-Hexyl-benzenesulphonamide was prepared analogously to Example 1 by condensing benzenesulphochloride and n-hexylamine in the presence of water and sodium hydroxide solution. After complete conversion of the benzenesulphochloride, the resulting oil was, after acidification of the reaction mixture to pH 3, separated off from the aqueous phase, washed once more with water, a pH of 7 being established, and separated again from the aqueous phase. The crude product was worked up as indicated in Example 1. The N-n-hexyl-benzenesulphonamide obtained had a purity of 99.8% and a colour number of 5 Hazen.

50 or 100 ppm of 2-mercapto-benzimidazole were added with stirring to this N-n-hexyl-benzenesulphonamide, and the mixtures were then heated to 170° C. The colour numbers and extinction values were determined after and 3 hours. The heat stability of the N-n-hexyl-benzenesulphonamide without an additive was determined for comparison. All the values are listed in Table 8.

TABLE 8

(Example 8): Hazen colour numbers and extinction values (in brackets) of N—n-hexyl-benzenesulphonamide heat-treated at 170° C.

| No. | Quantity of 2-mercapto-benzimidazole | 1 hour | 3 hours |
|---|---|---|---|
| 8a | 100 ppm | 120 (0.030) | 270 (0.068) |
| 8b | 50 ppm | 440 (0.110) | >500 (0.215) |
| 8c* | none | >500 (0.335) | >>500 (1.021) |

*comparison test not according to the invention

EXAMPLE 9

N-2-Ethylhexyl-benzenesulphonamide was prepared analogously to Example 8 by condensing benzenesulphochloride and 2-ethylhexylamine in the presence of water and sodium hydroxide solution. After complete conversion of the benzenesulphochloride, the resulting oil was worked up as indicated in Example 8. The N-2-ethylhexyl-benzenesulphonamide obtained had a purity of >99.9% and a colour number of 5 Hazen.

50 or 100 ppm of 2-mercapto-benzimidazole were added with stirring to this N-2-ethylhexyl-benzenesulphonamide, and the mixtures were then heated to 170° C. The colour numbers and some extinction values were determined after 1 and 3 hours. The heat stability of N-2-ethylhexyl-benzenesulphonamide without additive was determined for comparison. All the values are listed in Table 9.

TABLE 9

(Example 9): Hazen colour numbers and some extinction values (in brackets) of N—2-ethylhexyl-benzenesulphonamide heat-treated at 170° C.

| No. | Quantity of 2-mercapto-benzimidazole | 1 hour | 3 hours |
|---|---|---|---|
| 9a | 100 ppm | 12 | 160 (0.040) |
| 9b | 50 ppm | 160 (0.040) | >500 (0.413) |
| 9c* | none | >500 (0.341) | >>500 (1.284) |

*comparison test not according to the invention

EXAMPLES 10–13

Analogously to Example 8, starting from benzenesulphochloride and, respectively, cyclohexylamine, 4-methyl-cyclohexylamine, n-decylamine and n-dodecylamine, the respective N-alkyl- and N-cycloalkyl-benzenesulphonamides were prepared. Their mixtures with 200 ppm of 2-mercapto-benzimidazole in each case showed a very good heat treatment behaviour as compared with the unstabilized compounds.

What is claimed is:

1. A composition comprising (i) one or more 2-mercapto-benzimidazole compound(s) of the formula $$R^1 \!-\!\!\left\langle\!\!\begin{array}{c}\phantom{x}\\\phantom{x}\end{array}\!\!\right\rangle\!\!\begin{array}{c} N \\ \| \\ \underset{\underset{H}{|}}{N} \end{array}\!\!C\!-\!S\!-\!X^1$$

wherein
R$^1$ denotes hydrogen or a C$_1$–C$_4$-alkyl group and X$^1$ denotes hydrogen or 1 equivalent of the metals Zn, Cd or Mn(II), in an amount of 10–1,000 ppm, relative to the total quantity of the composition, and
(ii) one or more N-alkyl-benzenesulphonamide(s), the alkyl group of which is open-chain C$_1$–C$_{12}$-alkyl or C$_5$–C$_7$-cycloalkyl and the benzene nucleus of which can be substituted by C$_1$–C$_4$-alkyl, said N-alkyl-benzenesulphonamides as the remainder makes up to 100% of the total quantity of the composition.

2. A composition according to claim 1, wherein the N-alkyl-benzenesulphonamide has an alkyl group having 1–8 C atoms or contains a cyclohexyl.

3. A composition according to claim 1, wherein the N-alkyl-benzenesulphonamide(s) is selected from the group consisting of N-n-Butyl-benzenesulphonamide, N-n-hexyl-benzene-sulphonamide and N-2-ethylhexyl-benzenesulphonamide.

4. A composition according to claim 1, containing one or more 2-mercapto-benzimidazole compound(s) of the formula

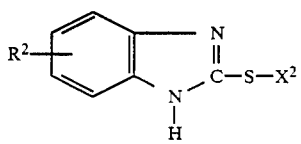

wherein
R² denotes hydrogen, methyl or ethyl and
X² denotes hydrogen or 1 equivalent of the metals Zn or Mn(II).

5. A composition according to claim 1, containing one or more 2-mercapto-benzimidazole compound(s) of the formula

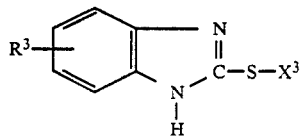

wherein
R³ denotes hydrogen or methyl and
X denotes hydrogen or ½ $Zn^{2+}$.

6. A composition according to claim 1, containing 15 to 300 ppm of the 2-mercapto-benzimidazole compound(s).

7. A composition according to claim 6, containing 15–200 ppm of the 2-mercapto-benzimidazole compound(s).

* * * * *